United States Patent
Ben-Nun

(10) Patent No.: US 7,172,601 B2
(45) Date of Patent: Feb. 6, 2007

(54) CATARACT SURGERY DEVICES AND METHODS FOR USING SAME

(75) Inventor: Joshua Ben-Nun, Moshay Beit Herut (IL)

(73) Assignee: Itos International Ltd., Wanchai (HK)

( * ) Notice: Subject to any disclaimer, the term of this patent is extended or adjusted under 35 U.S.C. 154(b) by 148 days.

(21) Appl. No.: 10/296,005

(22) PCT Filed: May 20, 2001

(86) PCT No.: PCT/IL01/00448

§ 371 (c)(1),
(2), (4) Date: Apr. 15, 2003

(87) PCT Pub. No.: WO01/89401

PCT Pub. Date: Nov. 29, 2001

(65) Prior Publication Data

US 2003/0158567 A1    Aug. 21, 2003

Related U.S. Application Data

(60) Provisional application No. 60/286,306, filed on Apr. 25, 2001, provisional application No. 60/205,554, filed on May 22, 2000.

(51) Int. Cl.
*A61B 17/32* (2006.01)
(52) U.S. Cl. ............ 606/107; 606/167; 606/170; 606/161
(58) Field of Classification Search ........ 606/20–31, 606/166, 170, 172, 107; 607/104, 141, 96–99, 607/113; 604/22, 521; 408/57, 59; 175/321; 166/244.1
See application file for complete search history.

(56) References Cited

U.S. PATENT DOCUMENTS

| | | | | |
|---|---|---|---|---|
| 3,971,383 A | * | 7/1976 | van Gerven | 606/23 |
| 3,976,077 A | * | 8/1976 | Kerfoot, Jr. | 606/107 |
| 3,996,935 A | * | 12/1976 | Banko | 604/22 |
| 5,019,036 A | * | 5/1991 | Stahl | 604/22 |
| 5,437,678 A | * | 8/1995 | Sorensen | 606/107 |
| 6,254,587 B1 | * | 7/2001 | Christ et al. | 604/521 |
| 6,328,747 B1 | * | 12/2001 | Nun | 606/107 |

* cited by examiner

Primary Examiner—Corrine McDermott
Assistant Examiner—Christopher D. Prone
(74) Attorney, Agent, or Firm—Edward Langer; Shiboleth Yiaraeli Roberts Zisman & Co.

(57) ABSTRACT

A surgical apparatus having a surgical tip, comprising: cooling means for freeze-sealing mammalian tissue, and control means, which control and induce coolant flow from coolant supply means, through a coolant outflow tube into an expansion chamber at the surgical tip. The temperature at the tip is thus lowered to a temperature at which mammalian tissue contacting the expansion chamber would adhere to the apparatus. The apparatus additionally comprises electrically powered heating means acting to raise and regulate the temperature of the apparatus; control means for activating the heating means, and power supply means. The apparatus is especially useful for surgery of tissue within a capsule, such as cataract surgery. In a preferred embodiment, the apparatus additionally comprises: a drill member coupled with a motor, an irrigation tube and an aspiration tube.

33 Claims, 14 Drawing Sheets

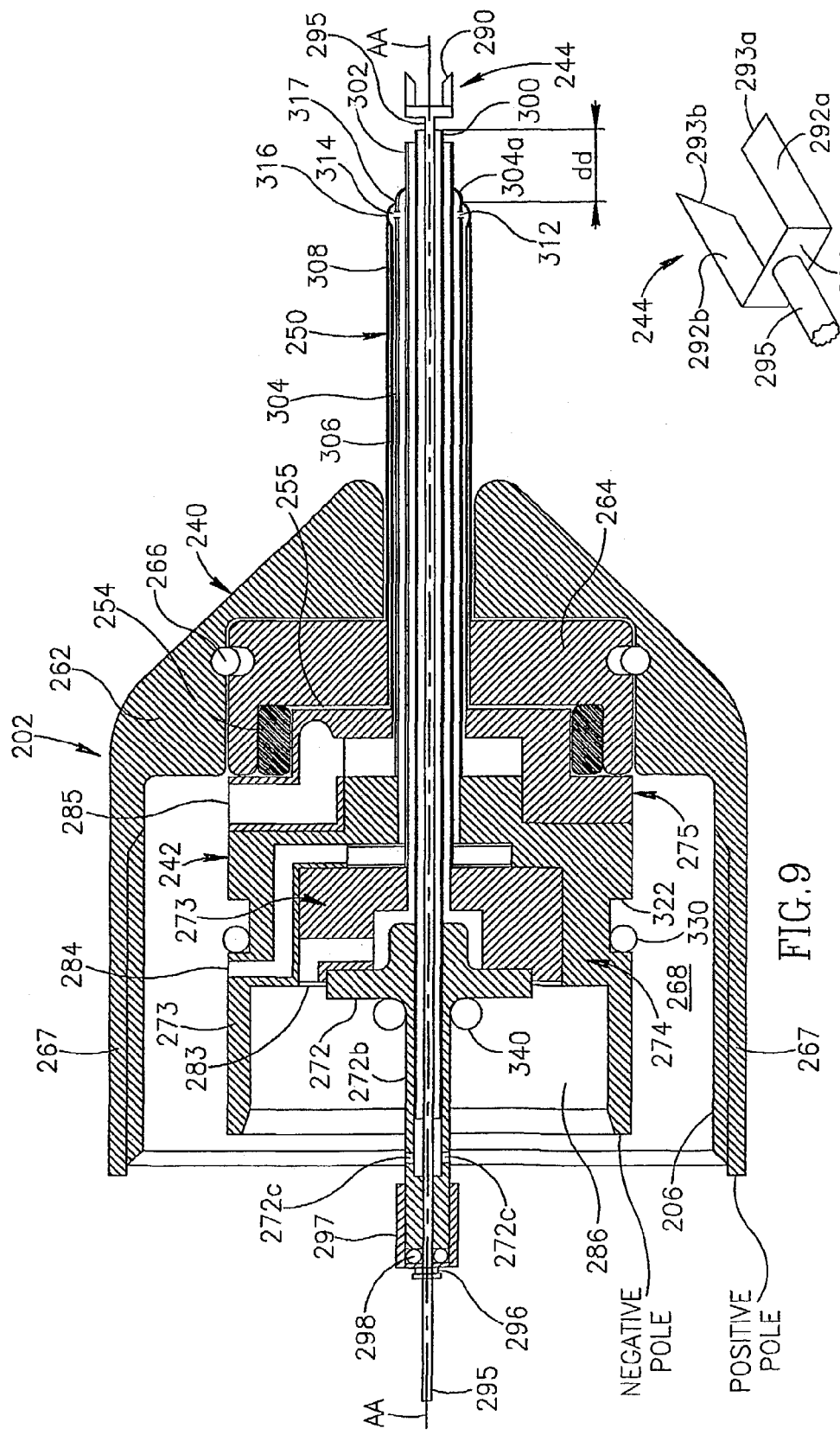

CATARACT SURGERY DEVICES AND METHODS FOR USING SAME

CROSS REFERENCES TO RELATED APPLICATIONS

This application claims priority from and is related to U.S. Provisional Patent Applications: 1) Ser. No. 60/286,306, filed Apr. 25, 2001, entitled: CATARACT SURGERY DEVICES AND METHODS FOR USING SAME; and 2) Ser. No. 60/205,554, filed May 22, 2000 and entitled: A METHOD AND A SYSTEM FOR PERFORMING CATARACT SURGERY. U.S. Provisional Patent Application Ser. No. 60/205,554 is related to U.S. patent application Ser. No. 09/156,982 filed Sep. 18, 1998 and entitled: A METHOD AND SYSTEM FOR PERFORMING CATATACT SURGERY, which is a continuation in part application of U.S. patent application Ser. No. 08/851,505, filed May 5, 1997 and entitled: A METHOD AND SYSTEM FOR PERFORMING CATATACT SURGERY, now U.S. Pat. No. 6,217,584. All four of these U.S. Patent Applications are incorporated by reference in their entirety herein.

FIELD OF THE INVENTION

The present invention relates to the field of devices for eye surgery in general and to the field of devices for cataract surgery in particular.

BACKGROUND OF THE INVENTION

Surgical removal of cataracts is well known in the art. In cataract surgery, the content of the eye lens is completely removed leaving only the posterior lens capsule, in which an artificial lens may be subsequently installed. It is appreciated that one of the main risks in cataract surgery is a potential damage, e.g. rupture, of the lens capsule. In the past, it was common practice to "freeze" the entire lens using appropriate means and then, to remove the lens in its entirety via a large opening which is formed in the cornea, specifically, along the Cornea Limbus. This procedure resulted in damage to the lens capsule and to the vitreous body and is, therefore, no longer in use Presently, there are a number of known methods for removing cataracts. FIG. 1 schematically illustrates a cross-sectional view of a human eye 10 during cataract surgery in accordance with one, commonly used, prior art method. A surgical instrument 12 and, optionally, a manipulation device 14, are inserted into eye lens 20 via cornea 16, a preferably dilated pupil 18 and an opening formed in the anterior capsule of lens 20. As is known in the art, lens 20 includes a core 28, known as the nucleus, which is formed of a relatively hard tissue. Nucleus or cataract 28 is surrounded by a layer 26 of relatively soft, gel-like tissue, known as the cortex, which fills lens capsule 24.

The soft tissue in cortex layer 26 is typically removed gradually using a vacuum suction device and/or a "scooping" device (not shown in the drawings). To remove nucleus 28, the hard tissue is typically, first, broken into small fragments and/or dissolved using appropriate instruments and/or solutions and is then removed gradually by suction and/or "scooping" as described above. Alternatively, the entire nucleus can be removed in one piece. However, this requires cutting a large opening in the cornea.

FIG. 1 illustrates one method of breaking a nucleus 28 using directional ultrasonic transmission. According to this method, instrument 12 includes a device 25, generally known as a Phacoemulsifier (Hereinafter: "Phaco"), which transmits intense ultrasonic energy into the nucleus 28. The crushing effect of the ultrasonic transmission of Phaco device 25 is typically enhanced by a stream of liquid 22 supplied from an external sleeve 23 of instrument 12, which liquid typically includes a dissolving agent. It is appreciated that, during surgery, a constant supply of liquids is generally required to compensate for escape of intraocular liquids and/or to assist in dissolving the content of lens 20. In the example shown in FIG. 1, the supply of liquid 22 via sleeve 3 is utilized both as a dissolving agent and as a compensatory liquid supply. However, it is appreciated that a separate liquid supply may additionally or alternatively be used.

Manipulation device 14 typically includes a thin, pointed instrument. For example, the thin pointed instrument can be a needle or a spatula, which provides partial counter-support to the operation of instrument 12 on nucleus 28. Such a device enables the surgeon to manipulate nucleus 28 by pushing it to a desired position and to temporarily support the nucleus at the desired position. However, it should be noted that the ability of the surgeon to manipulate and control nucleus 28 using device 14 is limited, due to various physical parameters. For example, the "angle of the attack" of device 14 on the traction between device 14 and the surface of nucleus 28 can be manipulated, using device 14, only by pushing and not by pulling.

Medical follow up studies reveal that the quality of the post-operative optical results depends on the size of the incision made during surgery, where smaller incisions are usually associated with better post-operative results.

An additional development favoring the reduction of the incision size is the availability of foldable artificial lenses, which can be introduced into the eye and inserted into the capsula while folded inside a needle-like device of relatively small diameter.

Unfortunately, ultrasonic systems such as the Phacoemulsifier are relatively expensive. Moreover, during the operation, the surgeon cannot observe a clearly defined border of the crushing action of the Phaco device 25. Thus, the inexperienced surgeon might inadvertently damage the posterior capsule of the lens, resulting in poorer post-operative results.

Additionally, the geometry of the crushing zone around the tip of the Phaco device 25 is not constant, and varies for different sonication intensities, while having no visible cue which the surgeon can use to determine the precise crushing range from the tip of the Phaco device 25.

Consequently, there is a steep learning curve for the surgeon, requiring a relatively long training period and resulting in lower quality of the post-operative results during the training period.

Furthermore, in certain cataract cases, the degree of hardening of the cataract nucleus 28 is such that the Phaco device 25 cannot crush it, thus, requiring the surgeon to broaden the small incision in order to remove the whole cataract nucleus.

SUMMARY OF THE INVENTION

The present invention seeks to provide an improved device for manipulating tissue during surgery. The manipulation device of the present invention is particularly useful in intraocular surgery, particularly in cataract removal surgery.

The present invention provides instrumentation for accessing the capsule of the lens, where the cataract (also known as the nucleus) resides. This instrumentation includes a cutting tool device for creating an opening of controlled dimensions in the capsule, a thermal probe for maintaining the integrity of this opening in the capsule, and a drilling unit for entering the capsule. This drilling unit is capable of dissolving the cataract within the capsule via turbulence energy therefrom. The dissolved cataract material can then be removed from the capsule by suction, typically through the drilling unit.

There is also disclosed a thermal probe with a thermally controlled torroidal end, that includes an opening dimensioned to accommodate the drilling unit, the torroidal portion configured to contact the capsule and maintain this contact by a freezing action upon the capsule and the cortex below. This gripping by freezing maintains the integrity of the capsule, by providing a tight seal to the opening, stabilizing it and rendering it free of shearing forces and leakage, during the procedure. Upon completion of the procedure, the torroidal portion is heated, to a temperature where the gripping by freezing is released and the drilling unit and thermal probe can be removed from the surgical site.

The above described procedure is typically performed under a pressure controlled air field, typically via a line placed under the cornea, intermediate the cornea and the capsule. This pressure controlled air field allows for additional external stabilization of the capsule during the procedure.

The present invention also provides a surgical apparatus with cooling, drilling and heating functions on a single instrument. The apparatus comprises a first tube including a proximal end and a distal end, a passageway for the inflow and outflow of coolant, this passageway comprising a second tube extending over at least a portion of the first tube, this second tube including a proximal end and a distal end, and providing for coolant inflow in the passageway. There is also a third tube extending over at least a portion of the second tube and including a proximal and a distal end, the distal end including at least one outwardly extending portion forming an expansion chamber for the coolant inside the third tube and for transferring cooling from the expansion chamber to outside of the third tube. This third tube also provides coolant outflow in the passageway. The second tube includes a bore at its distal end for coolant flow into the expansion chamber. There is fourth tube extending over at least a portion of the third tube, this fourth tube including a proximal end and a distal end and configured for communication with an electrical power source so as to heat when power from said power source is supplied to this fourth tube. This fourth tube is positioned to extend over at least a portion of the third tube to limit conduction of cooling, from the expansion chamber in the third tube, toward at least the proximal end of the third tube. The tubes are coaxial and dimensioned and positioned with respect to each other such that the distal end of the first tube extends beyond the distal ends of the second and third tubes, and that the distal ends of the second and third tubes extend beyond the distal end of the fourth tube.

There is also provided a method for surgery of tissue within a capsule, for example, a cataract within a lens capsule, the method comprising providing an apparatus. This apparatus comprises a conduit including a proximal end and a distal end, and it is configured for coolant transport. This conduit also includes a portion configured for concentrating cooling at the distal end. A drill member extends longitudinally through the conduit. This drill member includes a distal end and a drill bit at this distal end. There is also a tube having a proximal end and a distal end, that extends over the conduit in an arrangement, such that the distal end of the conduit extends beyond the distal end of the tube. The tube is configured for heating upon activation, to limit conduction of cooling from said conduit toward at least the proximal end of the conduit. Heating is such that temperatures within at least portions of the apparatus at least covered by the tube are within biocompatible ranges. An opening is created in the capsule and it is contacted by the portion of the conduit configured for concentrating cooling at the distal end. This conduit portion is cooled, such that sufficient cooling transfers to the capsule, causing an adhesion between tissue of the capsule and the apparatus, as the tissue typically cools so as to at least partially freeze, this adhesion allowing for gripping of the capsule by the apparatus in a controllable manner. The tube is then activated for heating, to limit conduction of cooling toward at least the proximal end of the conduit. At least a portion of the drill bit is then inserted through the opening into the capsule, and the drill bit is rotated, to speeds that create turbulence, so as to emulsify at least a portion of the tissue in the capsule. In cases where the tissue is a cataract and the capsule is a lens capsule, rotation typically continues until all of cataract is emulsified. The emulsified tissue or in some cases the emulsified cataract is removed via suction, also typically provided by the apparatus.

There is also disclosed a method for cataract surgery comprising, accessing a lens capsule having a cataract therein, at a surgical site and creating an opening in the lens capsule. A thermal probe, having at least a portion dimensioned to accommodate the opening is placed proximate to the periphery of the opening. The dimensioned portion of the thermal probe is cooled to a temperature such that the dimensioned portion temporarily adheres to the capsule, for providing the thermal probe with a controllable grip on the capsule. The cooling is maintained (confined) to an area proximate the opening by providing heat to the surgical site proximate to the opening. At least a portion, and typically all of the cataract is then emulsified. This emulsified cataract material can then be removed by suction.

BRIEF DESCRIPTION OF THE DRAWINGS

The invention will now be described with reference to the accompanying drawing figures, where like reference numerals or characters indicate corresponding or like components. In the drawings:

FIG. 9 is a cross sectional view of the tip of the apparatus detailed of FIG. 8;

FIG. 10 is a perspective view of the drill bit in accordance with the second embodiment of the invention;

DETAILED DESCRIPTION OF THE DRAWINGS.

Figure 1:
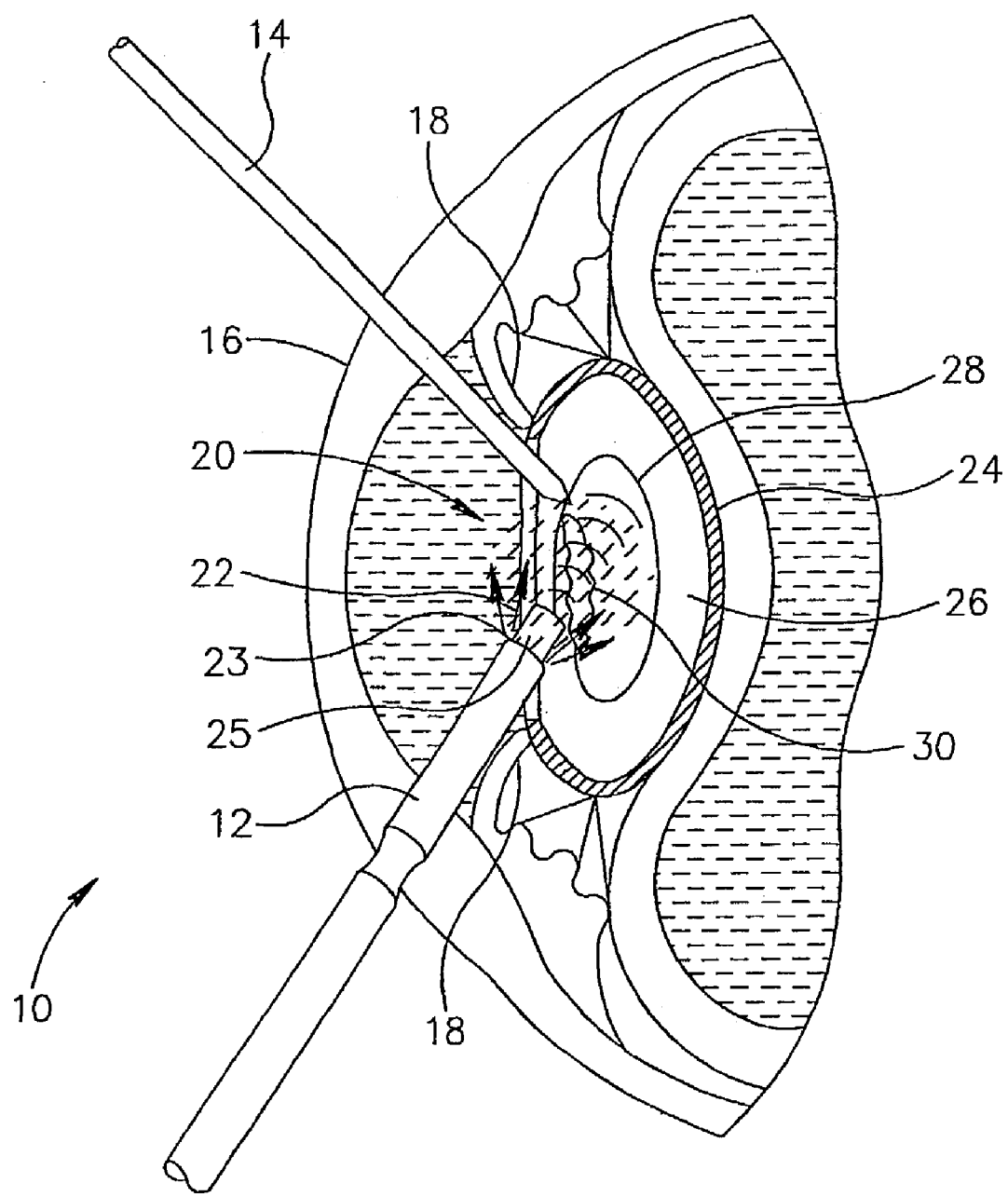
FIG. 1 is a schematic, side view, cross-sectional illustration of a human eye during cataract surgery in accordance with the prior art.
Figure 2:
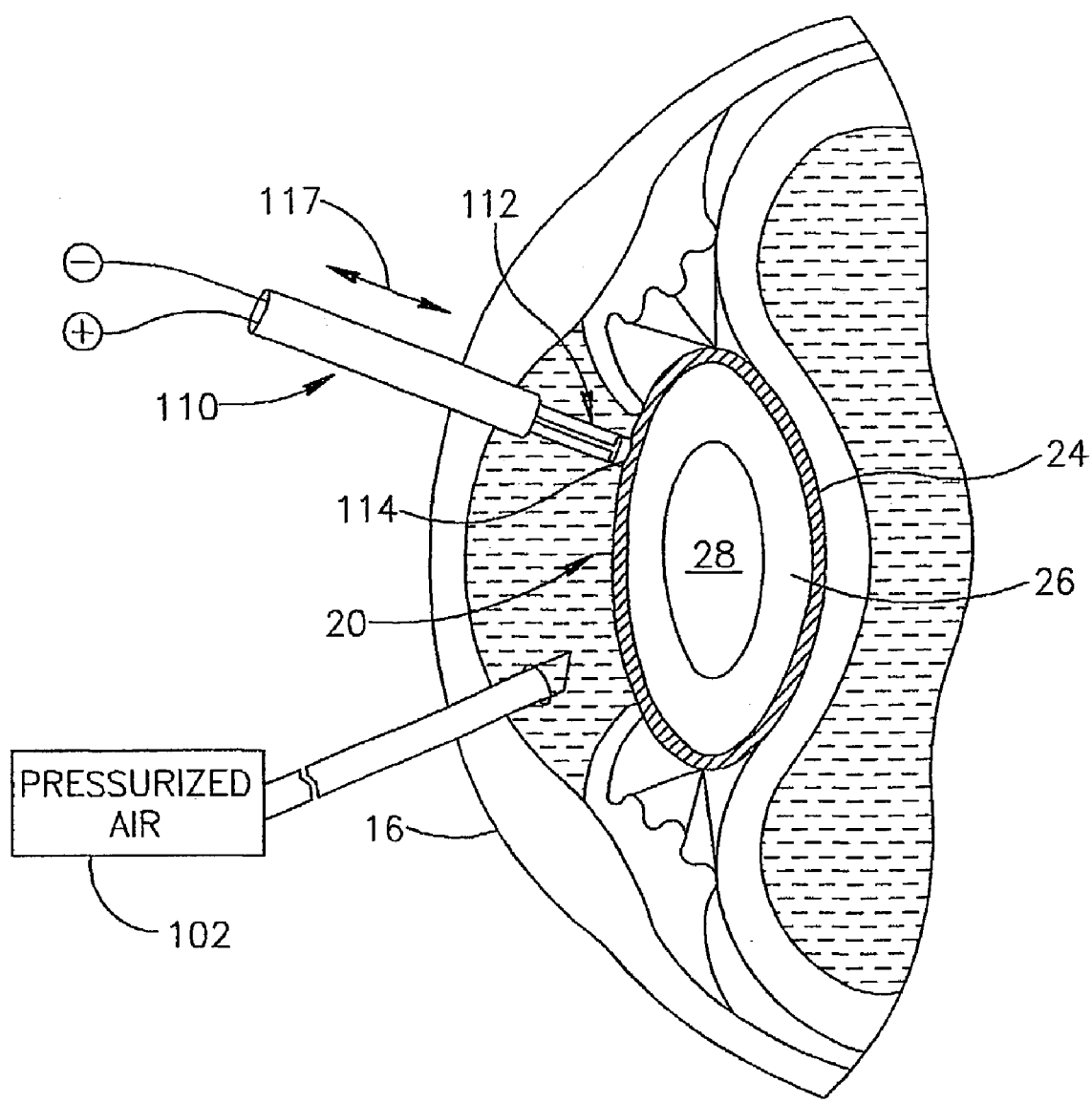
FIG. 2 is a perspective view of an embodiment of a thermal cutting tool of the invention in operation during a procedure in accordance with embodiments of the present invention.
Figure 3:
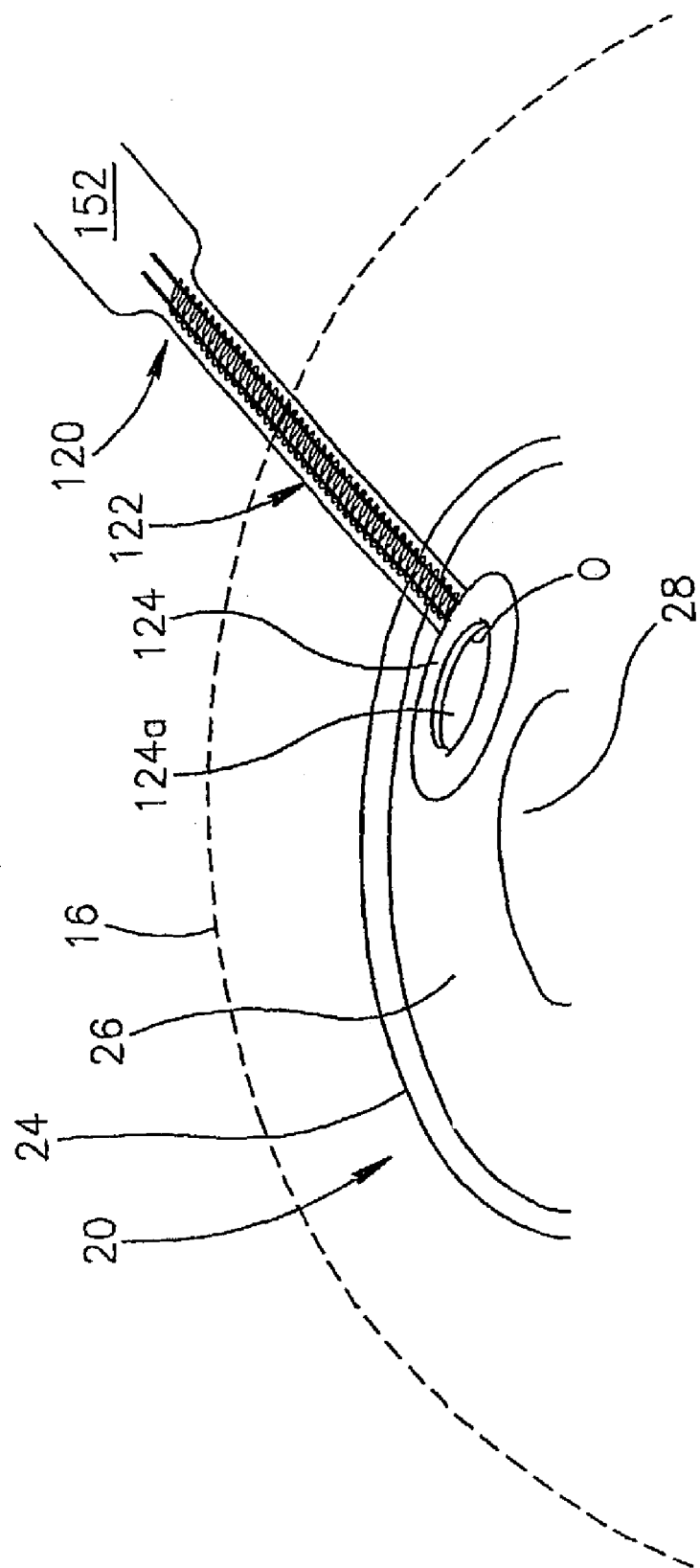
FIG. 3 is a perspective view of an embodiment of a thermal probe of the invention in operation during a procedure in accordance with embodiments of the present invention.
Figure 4:
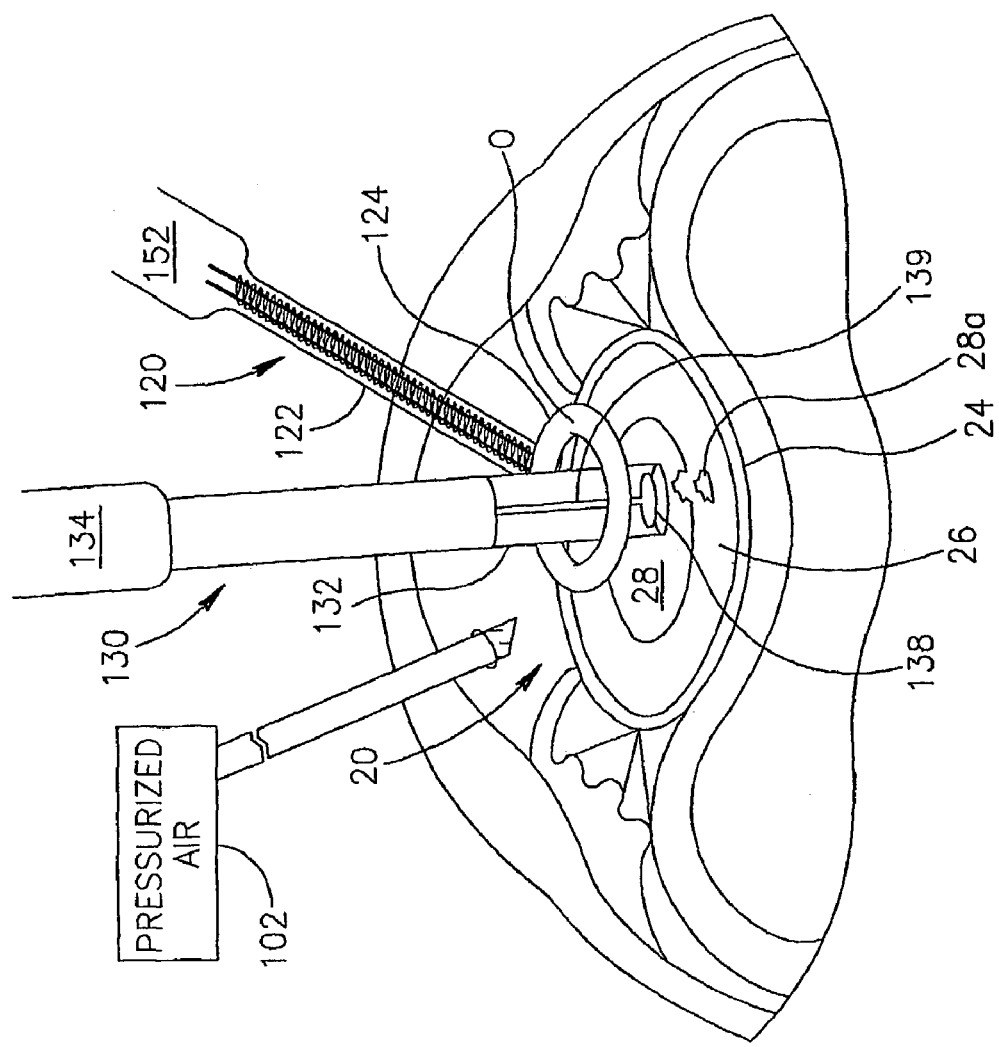
FIG. 4 is a schematic, side view, cross-sectional illustration of a human eye during cataract surgery using a the instrumentation and procedures in accordance with embodiments of the present invention.

FIGS. 2–4 show the instrumentation of the present invention performing cataract removal in accordance with the present invention. Initially, the area surrounding the lens 20 is placed under a pressurized air field from a pressurized air source 102. As shown in FIG. 2, a thermal cutting tool 110 (also shown in FIG. 5 and in additional detail below) is then maneuvered through an incision in the cornea 16, whereby its thermal portion 112, and in particular its beak or tip 114 contacts the lens capsule 24. An opening O (FIG. 3) is created in the lens capsule 24 by an electrical pulse through the tool 110 that creates a pulse of heat at the tip or beak 114. The pulse of heat concentrates at the tip or beak 114, as a result of the configuration of the slots 116 in the thermal portion 112. With the opening O now created in the lens capsule 24, the thermal cutting tool 110 is removed from the site, typically in the direction of the double headed arrow 117 (the insertion direction).

In FIG. 3, with the opening O now created, a thermal probe 120 (also shown in FIGS. 6 and 7A–7C and in additional detail below), is then maneuvered through a conventional made incision in the cornea 16. The thermal portion 122 of the thermal probe 120, specifically its torroidal portion 124, contacts the lens capsule 24 over and in alignment with the opening O.

As detailed specifically in FIG. 4, typically through the same corneal opening that was occupied by the thermal cutting tool 110, a drilling unit 130 of a Cataract Removing Device (CRD), the entire CRD detailed in commonly owned U.S. patent application Ser. Nos. 08/851,505 and 09/156,982, both disclosures of these patent applications incorporated by reference herein, and in particular its housing 132 enters the anterior chamber and the opening O, as the surgeon manipulates its handle 134.

The thermal probe 120 is now activated, specifically such that the torroidal portion 124, having an opening 124a, cools to a temperature where the capsule tissue adheres to the lower edge of the torroidal portion 124 and portions of the subcapsular cortex 26 below the capsule tissue also freeze. This results in the torroidal portion 114, having a firm freeze grip on the capsule 24. This freeze gripping is such that the integrity of this rounded opening is maintained, and specifically that a tight seal is provided to the opening, stabilizing the capsule 24 edges and rendering it free of shearing forces and leakage during the procedure. Typical cooling temperatures for the torroidal portion are approximately $-5C$. to $-10C$.

The drilling unit 130 can now be activated, as the surgeon, typically with handle controls, causes the drill bit 136 to move axially, such that the drill blade 138 at the end of the drill shaft 139 extend from the housing 132 and into the cortex 26. The drill bit 136 is rotated by motors (not shown) in the drilling unit 130 at speeds as to generate turbulence that decompose and dissolve the cataract (nucleus) 28 into pieces 28a and further to emulsify it into viscous particles within the cortex 26. These speeds may be, for example, approximately 100,000 rpm. During the rotation, irrigation and aspiration, both contemporaneous or non-contemporaneous, may be carried out through the housing 132. This procedure continues until the desired amount of nucleus 28, typically all of it, is emulsified and aspirated.

Upon completion of the procedure, the torroidal portion 124 is heated, typically by ceasing gas flow therethrough, to a temperature where the gripping by freezing is released and the thermal probe 120 and drilling unit 130 can be removed from the surgical site. A lens may then be implanted into the capsule 24 of the lens 20 by conventional procedures.

Figure 5:
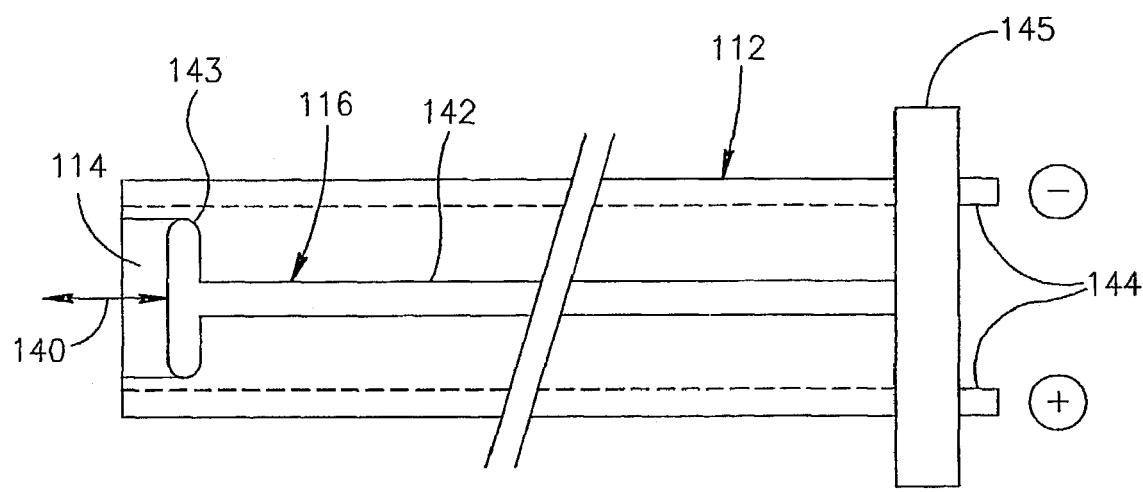
FIG. 5 is a side view of an embodiment of the thermal cutting tool housing in accordance with an embodiment of the preset invention.
Figure 6:
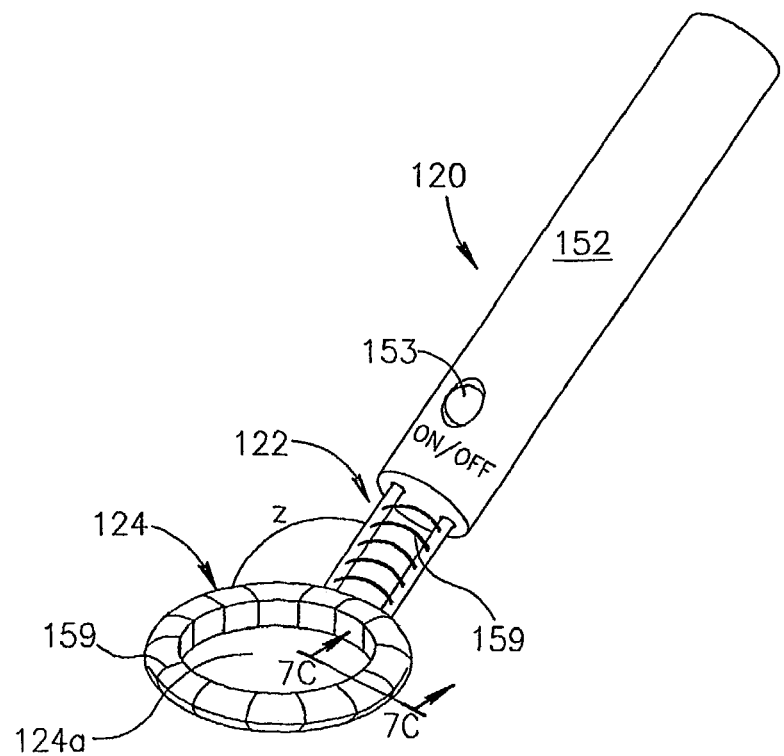
FIG. 6 is a perspective view of the thermal probe in accordance with an embodiment of the present invention.

FIG. 5 details the thermal portion 112 of the cutting tool 110. The thermal portion 112 is typically tubular, cylindrical in shape, although other shapes are also permissible. Slots 116 are oppositely disposed with respect to the axis (indicated by the double headed arrow 140). The slots 116 typically include a channel portion 142 continuous with a head portion 143, so as to be "T" shaped. This "T" shape is such that thermal load at the tip 114 will be maximized upon passage of electricity through electrical connectors 144 at the handle interface 145. The thermal portion 112 is of a conducting material, including metals such as steel, titanium or the like, that coupled with the "T" shaped slots 116 concentrates the heat at the tip or beak 114. The heat is typically received as energy pulses through the electrical connectors 144 at the handle interface 145.

Typically, there are two slots 116, equidistant from each other. One or three or more slots are also permissible, provided they are configured to concentrate the heat at the tip or beak 114.

FIGS. 6 and 7A–7C detail the thermal probe 120. This probe 120 includes a thermal portion 122 and terminates in a torroidal portion 124, with an opening 124a therein. A handle 152 attaches to the thermal portion 122 via heating 156 and cooling 157a, 157b connections (or ports) and there is a control system (not shown) along with associated mechanisms for providing heating and cooling to the thermal 122 and torroidal portions 124. There are also controls, activatable by the surgeon on the handle 152, including an on/off switch 158, and temperature controls, for the surgeon to control precise heating and cooling at the torroidal portion 124.

Heating is achieved via conduction (coils 159) that receive electricity from the heating connections 156. Cooling is achieved via gas circulation and expansion in the hollow chamber 160 of the torroidal portion 124. The gas is typically $CO_2$ (Carbon Dioxide) and $N_2O$ (Nitrous Oxide), released from a gas source (not shown) where these gasses are compressed, that cools upon expansion. Gas enters the thermal portion 122 through connection 157a and travels through a conduit 161 to a bore 161a, where it enters the torroidal portion 124. Gas leaves torroidal portion 124 through an outflow conduit 162, via a bore 162a. The outflow conduit connects to outflow lines (not shown) at connection 157b, where the outflow gas is discharged to the ambient environment.

Heating and cooling operate together, and as a result, cooling is localized at the torroidal portion 124 so at to be confined to the surface of the lens capsule 24, leaving the remaining environment at warmer temperatures, suitable for avoiding instrument and tissue damage from freezing.

The torroidal portion 124 is of a rounded triangular cross section, to enable smooth insertion of the housing 132 of the drilling unit 130 through the requisite opening O in the lens capsule 24. Other shapes are also suitable, provided, they can make a freezing contact with a significant amount of tissue, to properly freeze grip the tissue and maintain the sealing and integrity of the opening O, as detailed above. This the torroidal portion is at an angle "z" of anywhere for 0 to 45 degrees, and is typically approximately 30 degrees, with the torroidal opening 124a dimensioned to accommodate surgical openings, like opening O, that are typically approximately 1.0 to 2.0 mm.

The thermal portion 122 and torroidal portion 124 are typically an integral, one-piece member made of materials such as metals including stainless steel, titanium or the like. The materials may be bendable, such that the surgeon can adjust the thermal probe 120 prior to or during surgery.

Figure 7A:
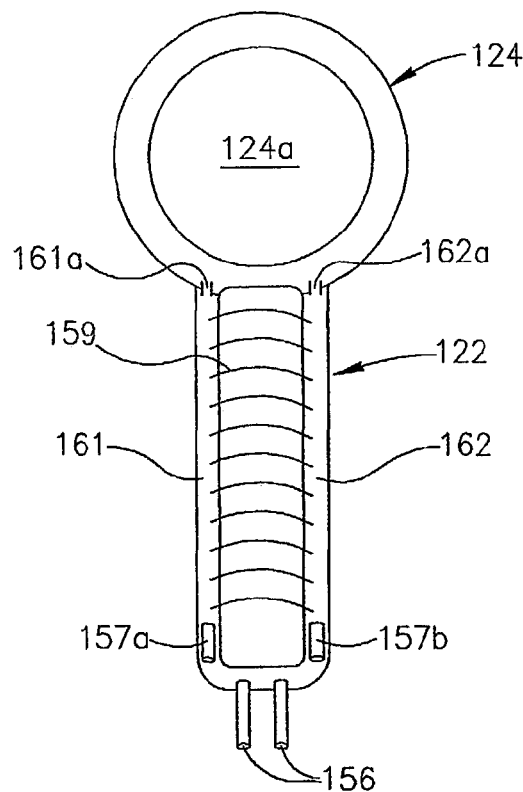
FIG. 7A is a cross sectional view of the thermal portion of the thermal probe of FIG. 6.
Figure 7B:
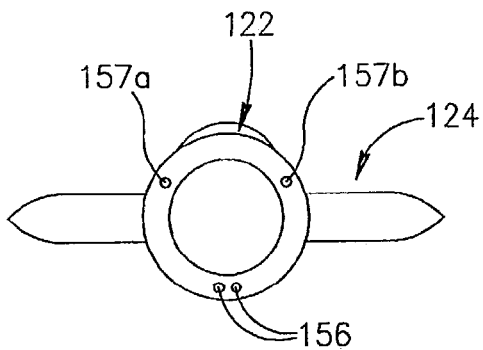
FIG. 7B is a rear view of the thermal portion of the thermal probe of FIG. 6.
Figure 7C:
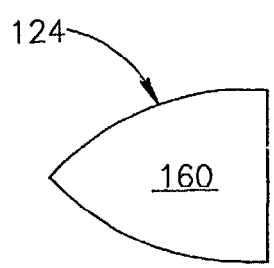
FIG. 7C is cross sectional view of the thermal portion of the thermal probe taken along line 7C—7C of FIG. 6.
Figure 7D:
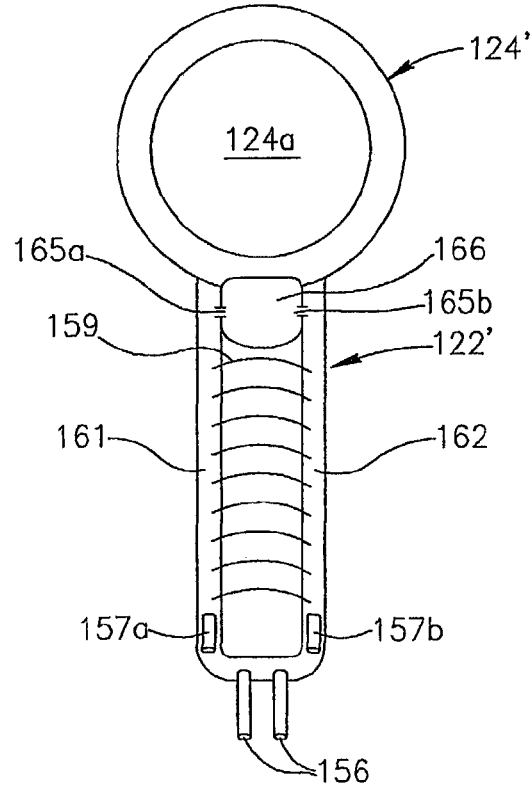
FIG. 7D is a cross sectional view of an alternate thermal portion for the thermal probe of FIG. 6.

Turning to FIG. 7D, there is shown an alternate embodiment of the thermal portion 122'. This thermal portion 122' is similar in all aspects to thermal portion 122, shown in FIGS. 7A and 7B and described above, except as described hereinbelow. Specifically, in this thermal portion 122', the torroidal portion 124' is a solid member (otherwise similar in all aspects to torroidal portion 124 as shown and detailed above, except where indicated below), made of a thermal (cool) conducting material such as gold, or other good thermal (cool) conductor. It is joined to the remainder of the thermal portion 122' by conventional metal joining techniques. Between gas supply 161 and gas outflow 162 conduits is a chamber 165 in contact with the torroidal portion 124'. Bores 166a, 166b connect the respective gas conduits 161, 162 with the chamber 165.

The chamber 165 serves as an expansion chamber for the incoming gas, allowing it to cool. This cooling is transferred to the torroidal portion 124', that because of its good conduction, allows for cooling to spread rapidly over the entire torroidal portion 124'. Cooling is thus similar to that described above and this thermal portion 122' operates identically to thermal portion 122.

This surgical procedure and the tools associated therewith allows the capsule to remain intact during the entire surgical procedure.

Figure 8:
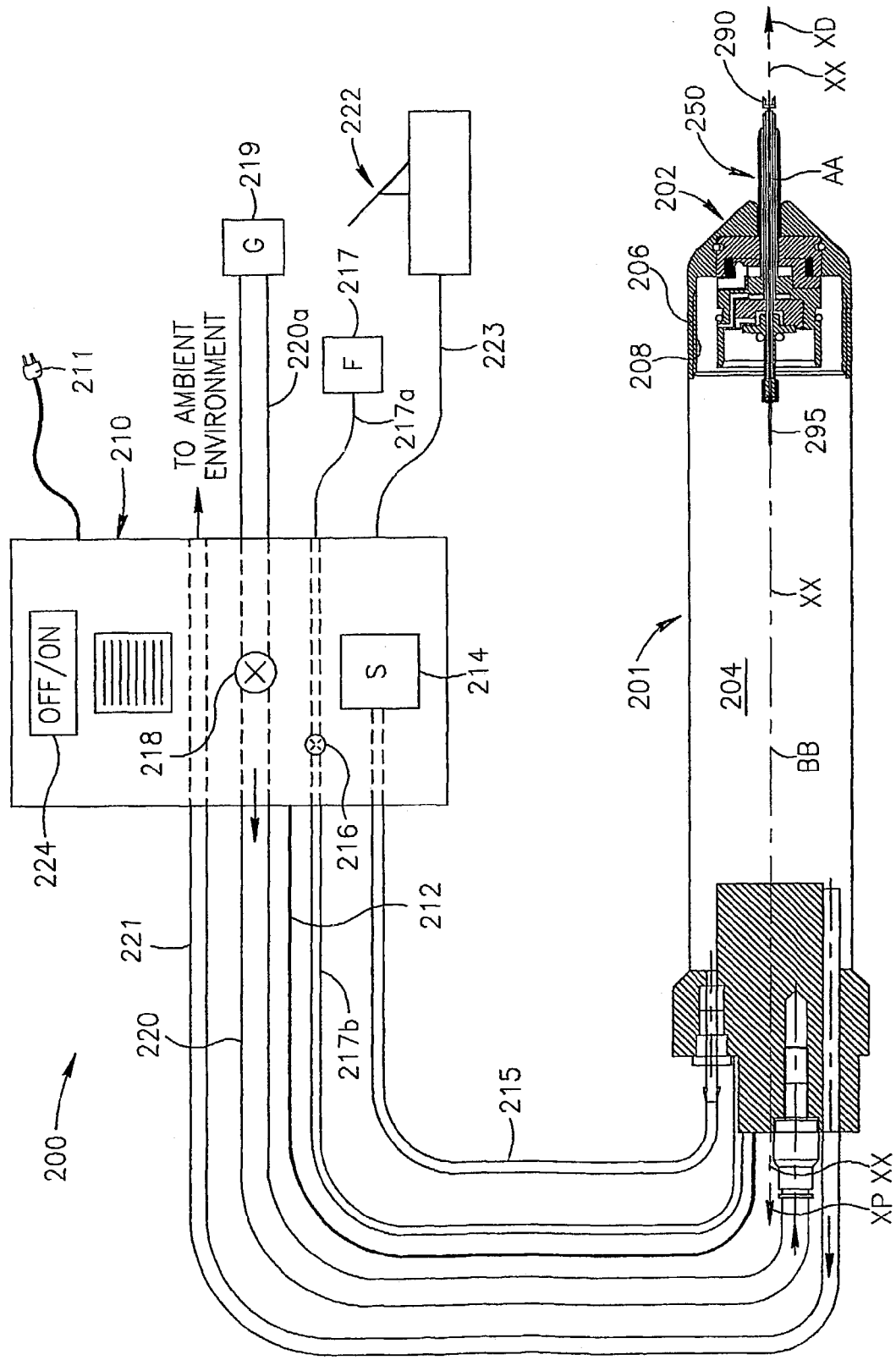
FIG. 8 is a perspective view of a system and apparatus in accordance with a second embodiment of the invention.

Turning now to FIG. 8, there is shown a system 200 in accordance with a second embodiment of the invention. The system 200 includes an apparatus 201 where the thermal (heating/cooling) and drilling functions, detailed above, have been consolidated in a single instrument.

The apparatus 201 includes a tip 202 and a handle 204. The tip 202 is typically disposable and is removable from the handle 204. An axis XX extends through the apparatus 201, and is coaxial with both axis AA (also shown in FIG. 9) extending through the tip 202 and axis BB (also shown in FIG. 11) extending through the handle 204, when the apparatus 201 is properly assembled. For purposes of description and orientation of components for the system 200, and typically the apparatus 201, the terms "proximal" and "distal" will be employed, whereby "distal" is in the direction of the tip 202 and more particularly in the direction indicated by arrow head XD on axis XX, and "proximal" is in the direction of the handle 204 and more particularly in the direction indicated by arrow head XP on axis XX.

The tip 202 engages the handle 204 by threads 206, 208 correspondingly configured on the tip 202 and handle 204 or other similar cooperating arrangement. The apparatus 201 is controlled by a control unit 210, that connects to a power source (not shown), such as an electrical outlet or the like via a plug 211 or the like. The control unit 210 provides power to the handle 204 through electrical lines 212. There is a suction unit (S) 214, inboard the control unit 210, but it could also be outboard of the control unit 210, to provide suction to the handle 204 and tip 202 through suction line 215. The control unit 210 also includes a valve 216 to control the flow of irrigation fluid, from a fluid source (F) 217 (through a line 217a), to the handle 204 and tip 202, through fluid line 217b. There is another valve 218 to control gas flow to the handle 204 and tip 202, from a gas source (G) 219, through a gas line 220 (the gas source 219 connecting to the valve 218 via line 220a). The gas or coolant source 219 is typically of compressed gases, that cool upon expansion, such as, for example, $CO_2$ (Carbon Dioxide) and $N_2O$ (Nitrous Oxide). There is also a gas outflow line 221, connected to the handle 204, from which gas is discharged to the ambient environment.

A foot switch 222 (detailed below in FIGS. 17 and 18) is electrically connected to the control unit 210 by a line 223, and controls many functions of the above detailed system 200. There is also an ON/OFF switch 224 on the control unit 210 that controls power to the control unit 210 and the foot switch 222.

Turning also to FIG. 9, there is shown the tip 202, that is formed of a head portion 240, and a core 242, and supports a drill member 244, housed in a series of overlapping tubes 250 with spaces therebetween, that are mounted in the head portion 240 and core 242 respectively. The core 242 is separated from the head portion 240 by a ring of electrical insulation 254, and an air gap 255, such that the head portion 240 and core 242 do not contact each other and thus, can maintain different electrical potentials to form an electrical circuit (detailed below).

The head portion 240 is typically formed of two members, an outer member 262 and an inner member 264 with an O-ring 266 therebetween, of materials such as conductive polymers or other similar materials, to provide shock absorbance of from vibrations, due to the high rpm speeds of the drill member 244 (typically approximately 80,000 rpm). The outer member 262 includes an extended portion 267, and a chamber 268 is present between the extended portion 267 that envelopes the core 242. This extended portion 267 typically include threads 206 on its inner side, that correspond with threads 208 on the handle 204, so as to allow joining and retaining of the tip 202 on the handle 204 when use of the apparatus 201 is desired. The head portion 240 is typically formed of surgical grade steel, other biocompatible metal or other biocompatable material, provided these materials are electrical conductors. Plastic with electrically conducting wires therein is also suitable.

The core 242 is formed from collars 272–275, and supports tubes (detailed below), that protrude from the head portion 240. The collars 272–275 are configured to provide passages 283–285 for suction, fluids and gases into the respective tubes (detailed below), from the respective tubes 530, 540, 550, 552, 560 in the handle 204 (detailed in FIGS. 14–16, and detailed below). The three inner collars 272–274, form a space 286 dimensioned for receiving a stub 420 on the handle 204.

Turning also to FIG. 10, the drill member 244 is formed of a drill bit 290, with balanced blades 292a, 292b having oppositely tapered ends 293a, 293b, connected to a crossbar 294. While two balanced blades 292a, 292b with oppositely tapered ends 293a, 293b are shown, this is exemplary only, as the drill bit 290 could be modified to support any number of balanced blades, with any end tapering arrangements, provided the drill bit 290 is able to rotate in a balanced manner. Alternately, the drill bit 290 can be in accordance with lens-reducing head, as disclosed (as element 318 and shown in one instance in FIG. 4d) in U.S. Pat. No. 5,690,641 (Sorensen, et al.), this disclosure incorporated by reference herein.

The drill bit 290 is mounted on a shaft 295, that extends beyond the head portion 240, that is received by the handle 204. Moving in the proximal direction, prior to the terminal end of the shaft 295, there is a circumferential protrusion 296, that abuts a stop collar 297, that receives the proximal end 272a of the innermost core collar 272, with an O-ring 298 therebetween for shock absorbence and inhibiting friction between the core collar 272 and the stop collar 297.

The drill bit 290 and shaft 295 are made of biocompatible metal such as titanium, stainless steel or the like. The drill bit 290 may be a single piece, or the blades 292a, 292b, and crossbar 294 can be single pieces joined together by conventional metal joining techniques such as welding or the like. The drill bit 290 is joined (at the crossbar 294) to the shaft 295 by conventional metal joining techniques such as welding or the like.

The series of tubes 250, is formed by tubes 300, 302, 304, 306, 308, that are typically concentric and coaxial (with respect to axis AA), so as to properly accommodate the drill member 244 and allow for the respective ingress and egress of fluids, gases and particulates. These tubes 300, 302, 304, 306, 308 are made of surgical grade steel or any other biocompatable metal or other biocompatible material, provided that these materials are electrical conductors.

The innermost or central tube 300 serves as a housing for the drill shaft 295. This tube 300 also provides a passage for suction of fluids, particulates, etc. from the surgical site. It is mounted in the innermost core collar 272. This collar 272 includes a proximal end 272a and a distal end 272b. The proximal end 272a is tubular and is received in the stop collar 297 and abuts the O-ring 298. This proximal end 272a also includes at least one bore 272c (two are shown) through which suction can be brought to the central tube 300.

Moving outward, the second tube 302 is a tube through which fluid is transported to the surgical site. This tube 302 terminates just slightly proximal with respect to the end of the central tube 300. It is mounted in an intermediate core collar 273 in a manner that fluid can pass from the passage 283 in the core collar 273 to the tube 302.

Alternately, the functions of the tubes 300, 302 can be switched. In this case, tube 300 would supply fluid to the surgical site while suction would be provided through the second tube 302. The reminder of the apparatus 201 would be modified accordingly to accommodate this change in tubes 300, 302.

Continuing outward, the third tube 304 and fourth tube 306, when coupled with the requisite spaces/passages/channels/canals in the collars in the tip 202 and in the handle 204, respectively, gas source 219 and gas lines 220, 220a, 221 and controller 210 form a cooling system, that is closed to the ambient environment. Inner tube 304 is a gas transport tube having a lumen in communication with coolant gas source 219, while outer tube 306 is an outlet tube, through which the gas returns to the apparatus 201. Both tubes 304, 306 are closed to the environment as the distal end 304a of the inner tube 304 is rounded, so as form a closed space with the second tube 302. This tube 304 includes at least one bore 312, two are shown here, that allow gas to pass from the lumen of this tube 204 into an expansion chamber 314 of the outlet tube 306.

The expansion chamber 314 receives gas through the bores 312. This expansion chamber 314 is typically formed by an outwardly protruding arced circumferential portion 316, that closes on the inner tube 304, at or near the distal end 304a. This arced portion 316 creates space for expansion of the gas, to create cooling on the outside side of the arced portion 316. These two tubes 304, 306 terminate at approximately the same point, proximal to the second tube 304. The arced circumferential portion 316 coupled with the rounded distal end 304a of the supply tube 304 define a shoulder 317 along the outer side. This configuration confines cooling to the portion of the shoulder 317 formed by at least the arced. portion 316 (but typically also includes the other portion of the shoulder 317 formed by the rounded distal end 304a of supply tube 304), so as to have localized cooling. This cooling is localized and at temperatures sufficient to freeze the requisite tissues upon contact with the shoulder 317, and here for example, allowing for gripping or freeze gripping of the capsule 24, without harming any additional tissues. Additionally, the termination of tubes 304 and 306, forming the shoulder 317 is of a larger diameter than inner tubes 300, 302 and coupled with a distance, indicated by dd (typically approximately 0.5 mm), between the shoulder 317 and termination of innermost tube 300, the penetration depth of the drilling unit 244 into the requisite tissue is limited, here for example, the penetration depth into the capsule 24. This allows for maximum safety and effectiveness of the rotating drill blades 292a, 292b.

Tube 304 is mounted in an intermediate core collar 274 in a manner where coolant gas can pass from the passage 284 into the core collar 274 to the tube 304. Similarly, tube 306 is mounted in an outer core collar 275 in a manner where coolant gas can leave the tube 306 by a passage 285 in the collar 275.

The outermost tube 308 is a heater tube. It contacts the expansion tube 306 at its (the heater tube's 308) distal end. Coupled with the expansion tube 306 mounted to a collar 275 of one potential, for example negative, and the outermost tube 308 is mounted on the inner member 264 of the head portion 260 of another potential, for example, typically positive, an electrical circuit is formed. This arrangement is such that when power is received, the outermost or heater tube 308 will become heated. This heating is such that it at least partially confines or localizes the cooling from the gas tubes 304, 306, to the surgical site, at or near the outer side of the expansion chamber 314, while keeping temperatures in the tubes 300, 302, 304, 306 or portions thereof, over which the heater tube 308 extends, within a biocompatible range. This heating limits any backwards conduction of cooling temperatures from the expansion chamber 314, so as to avoid any tissue damage, for example to the cornea 16, iris and other surrounding tissues, from this cooling.

The core 242 and in particular its collars 272–275 are typically formed of surgical grade steel, other biocompatible metal or other biocompatable material, provided these materials are electrical conductors. An O-ring 330 typically surrounds the core 242, at its intermediate collar 274, that includes a circumferential indent 332 to accommodate this O-ring 330. An O-ring 340 also surrounds the innermost core collar 272 at its distal end 272b. These O-rings 330, 340 are made of elastomers or any other materials suitable for sealing and shock absorbence and friction reduction, from correspondingly configured components on the handle 204 (detailed below).

Figure 11:
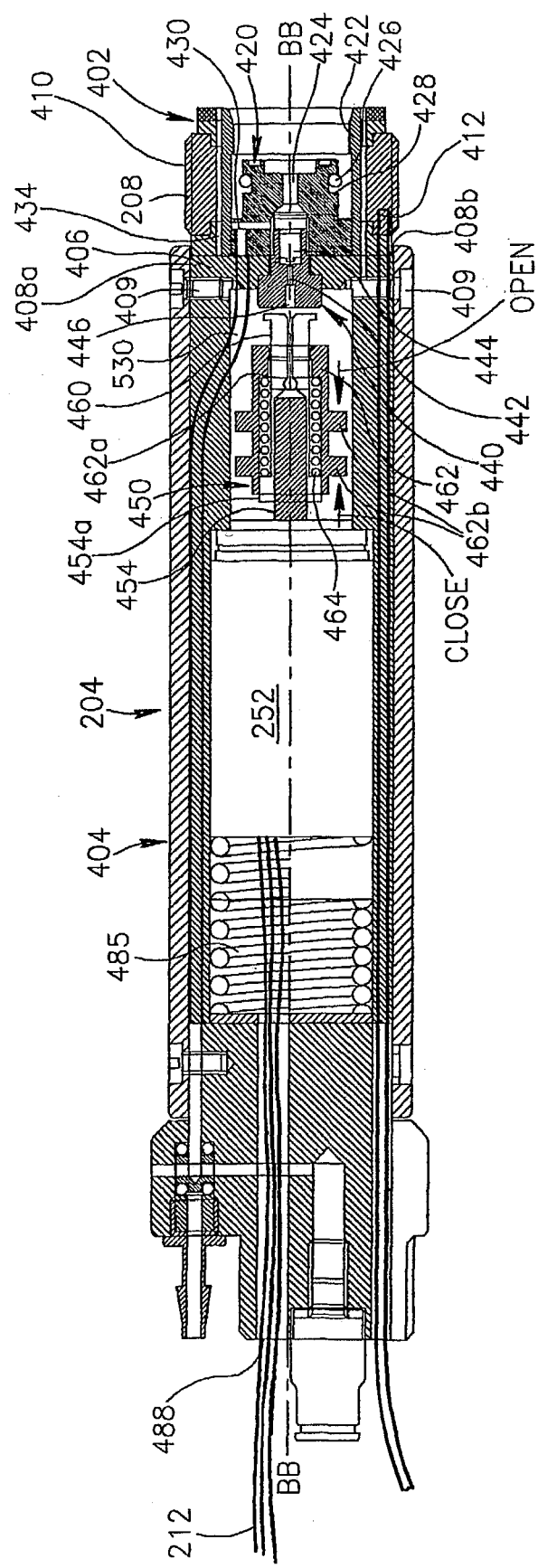
FIG. 11 is a cross sectional view of the handle in accordance with the apparatus detailed in FIG. 8.

FIGS. 11–16 show the handle 204 in detail. Turning to FIG. 11, this handle 204 is formed by a head portion 402, a body 404 and a front plate 406. An axis BB extends through this head portion 402 and body 404, such that it is in alignment with Axis AA of the tip 202, when the tip 202 and handle are joined together. The head portion 402 connects to the body 404 by being screwed into the body 404, via corresponding threads 408a, 408b on the head portion 402 and body 404 respectively, and/or is attached to the front plate 406, by conventional attachment techniques and mechanisms. The handle also includes screws 409 that hold components in place.

The head portion 402 includes an outer ring 410, typically having threads 208 on its outer side, or other locking mechanism, corresponding with the threads 206 or other locking mechanism on the tip 202 at the extended portions 267. This outer ring is typically made of surgical grade steel or other biocompatible material, that is an electrical conductor, for in accordance with the head portion 240 of the tip 202, this outer ring 410 also has a positive potential, to form a portion of the electrical circuit, as detailed above. An electrical supply line 412 contacts the outer ring 410, supplying it with electricity to provide the electrical potential, here for example, positive potential.

The head portion 402 also includes a stub 420 with a circumferential cylinder 422 around it, for engaging the collars 272–275. The stub 420, fits within the space 286 formed by the inner collar members 272–274. The stub 420 includes a central bore 424 for receiving the drill shaft 295 and stop collar 297, along with an O-ring 426 (in accordance with those O-rings detailed above) in a circumferential indent 428, for shock absorbence and friction reduction when the tip 202 and handle 204 are joined together. A passage 430 that receives a tube 530, that extends through the handle 204, which supplies suction is also in the stub 420 and extends to the central bore 424.

The cylinder 422 is dimensioned to extend into the chamber 268, as far as but not covering gas outflow passage 285 in core collar 275. Accordingly, the space 434 between the cylinder 422 and the outer ring 410 provides a portion of the passage for gas return.

The stub 420 and front plate 406 couple to hold a retainer 440. The retainer 440 includes a bore 442 extending axially therethrough (along axis BB), with this bore including a distal chamber 444 and a tail portion 446. The distal chamber 444 is correspondingly configured to seat the stop collar 297. This distal chamber 444 is slightly larger in dimensions than the stop collar 297, to allow its rotation therein and includes an O-ring 248 (in accordance with the O-rings detailed above) at its proximal end for shock absorbenace and friction reduction. The tail portion 446 is of a diameter larger than that of the shaft 295, but of a diameter sufficient to allow shaft 295 rotation in a balanced manner.

A shaft holding unit 450 is connected to a motor 452 by a drive rod 454. This shaft holding unit 450 receives and holds the remaining end of the shaft 295 (that portion proximal to the stop collar 297) so as to be rotated by the motor 452. The shaft holding unit 450 includes a clamping member 460, that is opened to receive the shaft 295 and closed to hold the shaft 295 for rotation, by an inner sleeve 462 that moves between distal and proximal positions to close and open the clamping member 460. A spring 464 that journals the drive rod 454 is typically biased so as to push the inner sleeve 462 distally, whereby the clamping member is in the closed position, holding the shaft 295 with sufficient retention to for rotation. The spring 464 is bounded by a proximal collar 454a of the drive rod 454 and an inwardly extending shoulder portion 462a on the inner sleeve 462.

Figure 12:
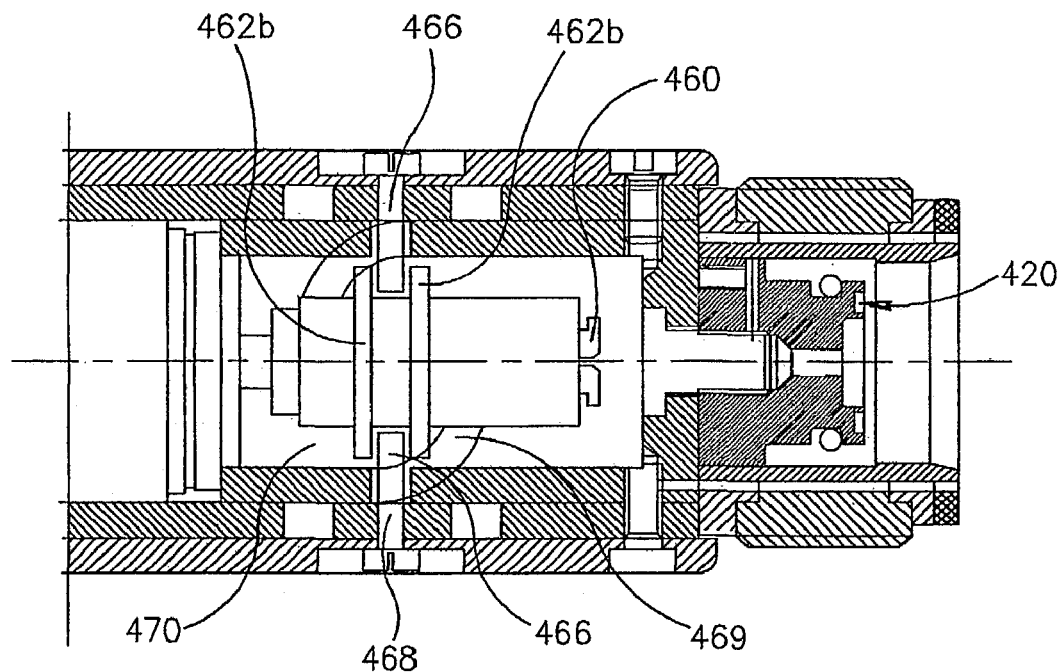
FIG. 12 is a cross sectional view of the shaft holding unit in accordance with the second embodiment of the invention, with the shaft removed.

Turning also to FIG. 12, circumferential rings 462b protrude from the inner sleeve 462 and abut teeth 466 of an outer sleeve 468 that travel in a fixed path, formed by grooves 469 in an intermediate sleeve 470. The outer sleeve 468 is moved, typically twisted, such that teeth 466 abut rings 462b, moving them. This moves the inner sleeve 462, ultimately opening and closing the clamping member 460 (around the shaft 295 in an engagement sufficiently tight for rotation) when desired.

The motor 452 is maintained in place by a spring 485. The motor 452 is typically a motor, capable of rotating the shaft at speeds of up to approximately 100,000 rpm, but here, for example, in this apparatus 201 motor speeds of approximately 80,000 rpm are typical. The motor 452 receives power from electrical lines 212, that extend into a canal 488 in the handle 204.

Figure 13:
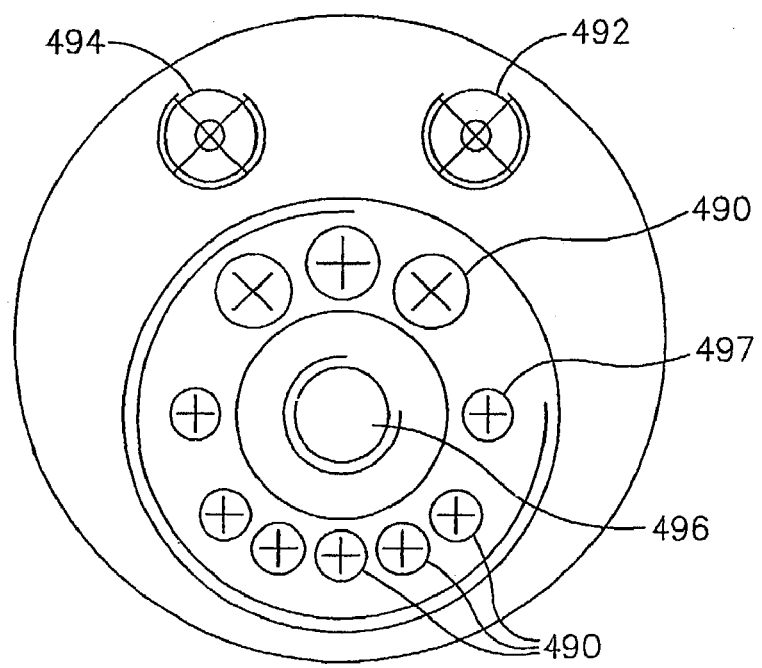
FIG. 13 is a rear view of the apparatus detailed in FIG. 8.

Turning now to FIGS. 13–16, and in particular FIG. 13, there is shown the rear or back of the handle 204. The handle 204 includes ports for various lines for electricity 490, suction 492, fluid ingress 494, gas inflow 496 and outflow 497.

Figure 14:
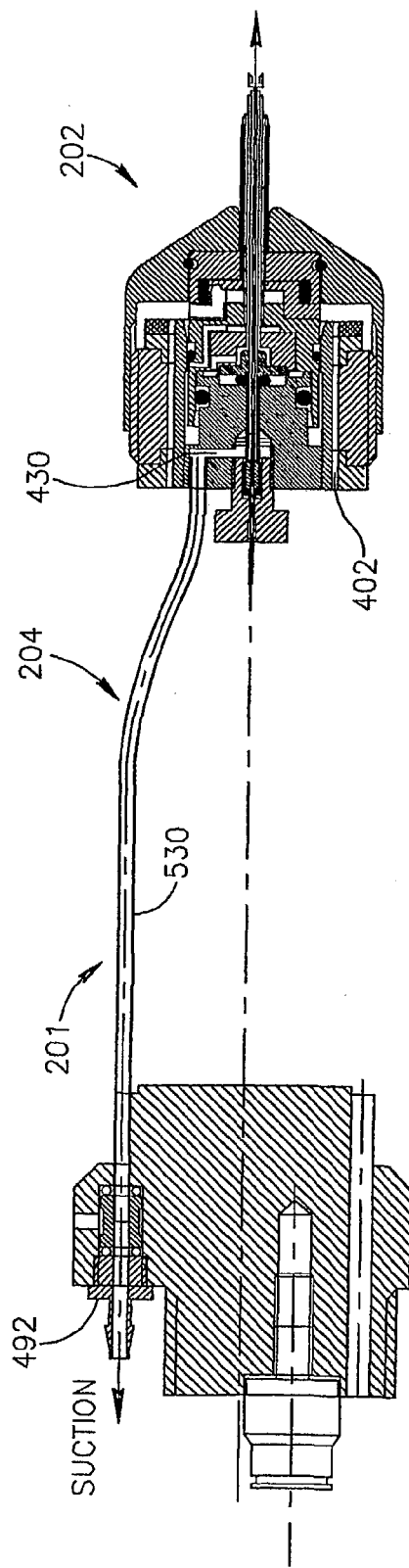
FIGS. 14–16 are cross sectional diagrams, detailing tube arrangements in the handle, at various rotations, of the second embodiment of the invention.

FIG. 14 shows the suction tube 530 in the handle 204. The suction tube 530 extends form the port 492 (where it receives suction from line 215 in FIG. 8) to the passageway 430 in the head portion 402 of the handle 204.

Figure 15:
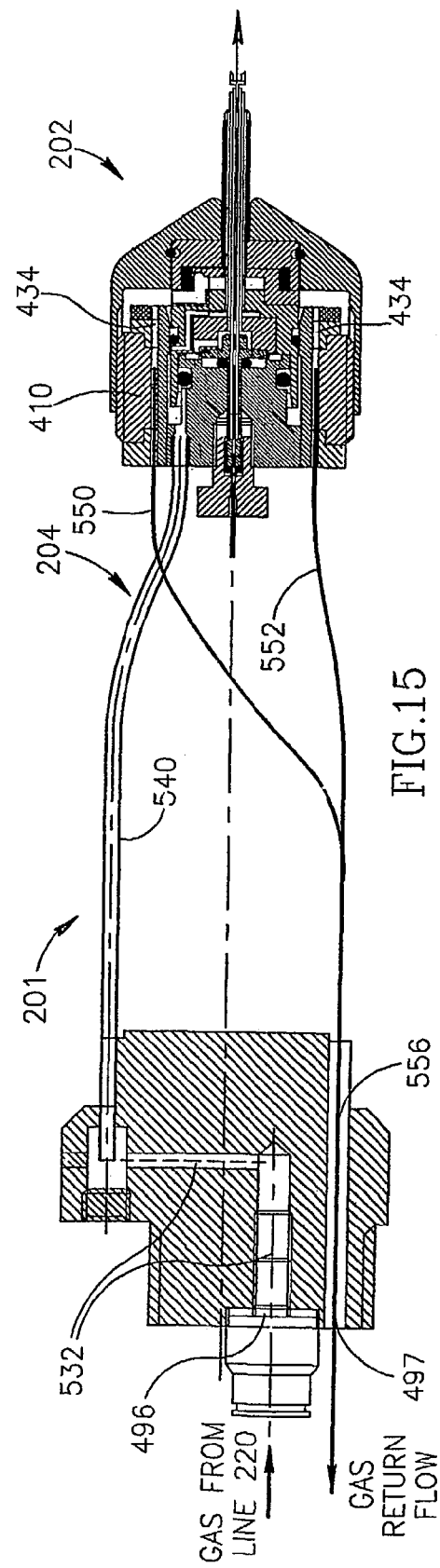

FIG. 15 shows gas inflow and outflow in the handle 204. Gas enters through port 496 in the handle 204, through gas line 220. This port 496 opens into a canal 532 in the handle 204, and then to a tube 540, through which gas enters the passage 284 (FIG. 9) in the core collar 274 (FIG. 9) prior to its entering gas supply tube 304 (FIG. 9). Gas outflow is through the passage 285 (FIG. 9) and into the space 434 between the cylinder 422 and outer ring 410 of the head portion 402 of the handle 204. From this space 434, gas flows through tubes 550, 552 (shown in broken lines) in the handle 204 to a canal 556 in the handle 204 and out through ports 497 to gas outflow lines 221 (FIG. 8).

Figure 16:
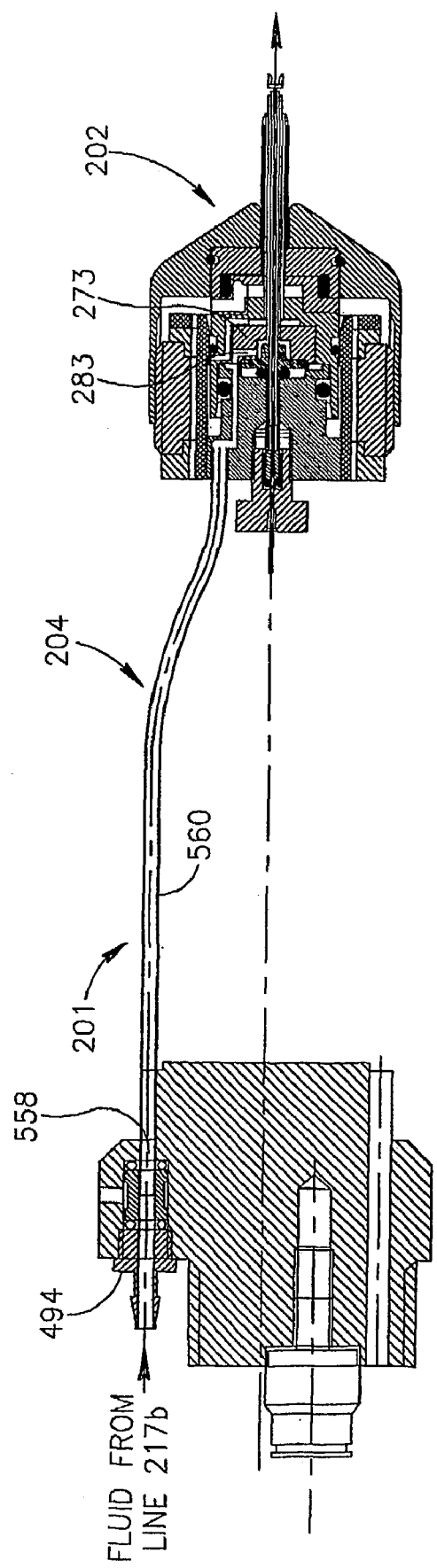

FIG. 16 shows fluid inflow in the handle 204. Fluid enters (from fluid line 217b, shown in FIG. 8) through port 494. This port 494 opens into a canal 558 in the handle 204, and then to a tube 560, through which fluid enters the passage 283 in the core collar 273 prior to its entering fluid supply tube 302 (FIG. 9).

Figure 17:
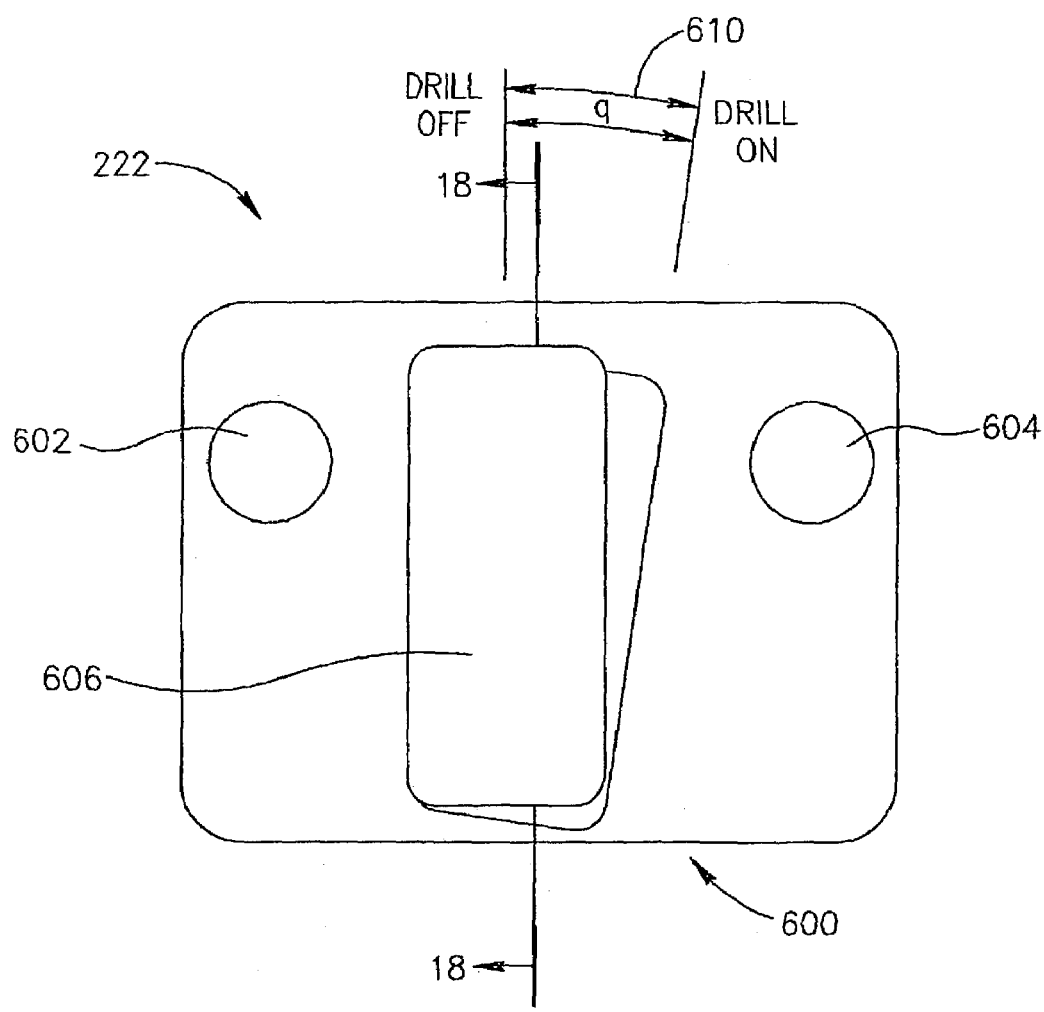
FIG. 17 is a top view of the foot switch of the second embodiment of the invention.
Figure 18:
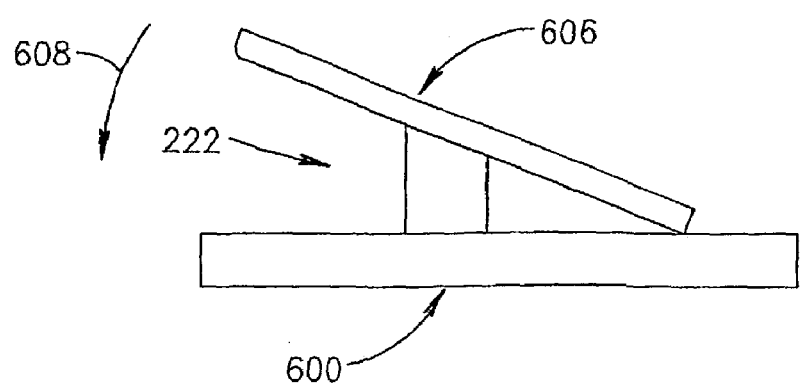
FIG. 18 is a cross sectional view of the foot switch of FIG. 17, taken along line 18—18.

FIGS. 17 and 18 detail the foot switch 222. The foot switch 222 includes a baseplate 600, with buttons for activating/ceasing coolant gas 602 and activating/ceasing fluid flow 604. These buttons 602, 604 are activated/deactivated by the surgeon stepping on them.

There is also a pedal 606, inclined, which the surgeon steps on to control suction. Suction ranges along a gradient, depending on how far down the pedal 606 is pressed (in the direction of arrow 608)—from no suction, when the pedal 606 is not depressed, to full suction when the pedal 606 is fully depressed. The pedal 606 can also be moved laterally, in accordance with double headed arrow 610, where drilling in OFF, when the pedal is perpendicular to the horizontal, or ON, when the pedal 606 has been moved angularly, corresponding to angle "q" with respect to the vertical.

In operation, the system 200, initially utilizes the procedure similar to that shown in FIG. 2 and described above. As a result of this initial procedure, an opening O', similar to opening O has been created.

Figure 19:
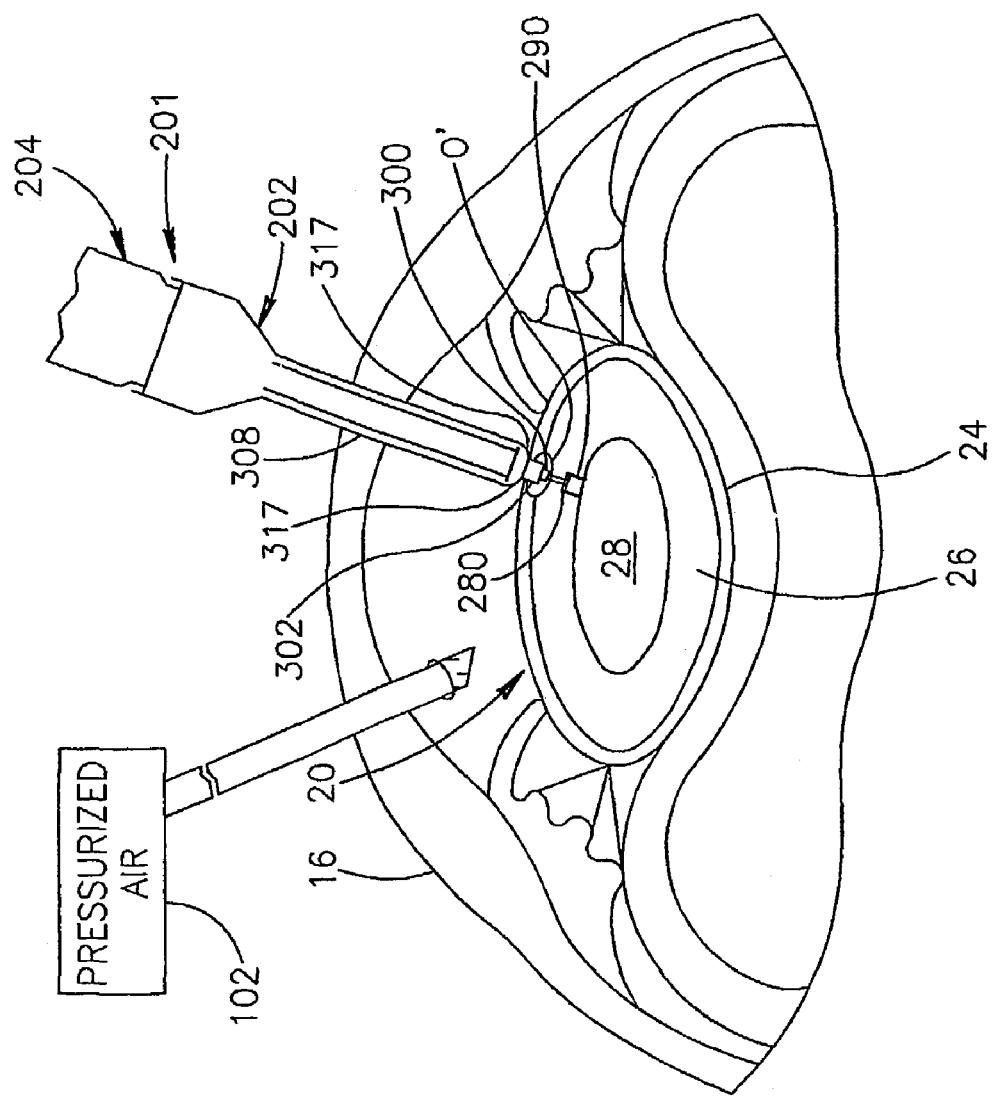
FIG. 19 is perspective view of the apparatus of FIG. 8 in an exemplary operation.

Turning now to FIG. 19, with opening O' now created, the thermal cutting tool (110 FIG. 2) is removed, from the site, as shown and described in FIG. 2. Typically through the same corneal incision (through which the thermal cutting tool was inserted and removed), the apparatus 201, in particular the tip 202 and more particularly, the overlapping tubes 250 are inserted into the corneal incision. Insertion continues into the lens 20, until the surgeon sees abutment of the shoulders 317 against the capsule 24. The drill bit 290, along with portions of central tube 300, having suction, and inner tube 302, with irrigation fluid, have entered the capsule 24 through opening O', and are in the cortex 26, while the shoulders 317 surround the opening O'.

The apparatus 201 is now activated, whereby the gas expands in the expansion chambers 314 to cool the shoulders 317 to a temperature, for example, approximately −5C. to −10C., whereby the shoulders 317 have transmitted cooling to the capsule 24, sufficient to freeze it, the freezing adhering at least portions of the shoulders 317 to the capsule 24, so the apparatus 201 has a controlling grip or freeze grip on the capsule 24. This freeze grip is such that the integrity of this rounded opening O' is maintained, and specifically that a tight seal is provided to the opening, stabilizing the capsule 24 edges and rendering it free of shearing forces and leakage during the procedure. Cooling is kept localized to the area of the capsule 24 contacting the shoulders, as the heater tube 308, heats to temperatures of approximately 25 C to 35 C to confine (localize) this cooling and keep the remainder of the surgical site and tip 202 at biocompatible ranges.

Drilling can now be activated, as the drill bit 290 rotates at speeds as to generate turbulence that decompose and dissolve the cataract (nucleus) 28 into pieces (identical to pieces 28a in FIG. 4) and further to emulsify it into viscous particles within the cortex 26 (as shown and described for FIG. 4 above). These speeds may be, for example, approximately 80,000 rpm. During the rotation, irrigation and aspiration, both contemporaneous or non-contemporaneous, may be carried out through the tubes 300, 302. This procedure continues until the desired amount of nucleus 28, typically all of it, is emulsified and aspirated, through suction tube 300.

Upon completion of the procedure, the gas flow is ceased, allowing the gripping by freezing of the shoulder 317 to be released. Once release is complete, the tip 202 (and thus the apparatus 201) can be removed from the surgical site. A lens may then be implanted into the capsule 24 by conventional procedures.

While the above described systems, apparatus and methods have been shown and described for cataract surgery, this is exemplary only. This is because without or with minimal modifications, these above described systems, apparatus and methods can be used for any kind pathology that involve encapsulated material to be removed while keeping the capsule intact at least during the procedure, to avoid spreading of the intracapsular content outside the capsule (into the surrounding tissue or blood stream). Such pathologies may be for example, encapsulated tumors, meniscus, encapsulated parasites, etc.

While preferred embodiments of the present invention have been described, so as to enable one of skill in the art to practice the present invention, the preceding description is intended to be exemplary only. It should not be used to limit the scope of the invention, which should be determined by reference to the following claims.

What is claimed is:

1. A surgical apparatus comprising:
   a housing, said apparatus having a proximal end and a surgical tip at its distal end, said housing containing therewithin:
      cooling means for freeze-sealing mammalian tissue, said cooling means extending from said housing to the surgical tip, said cooling means comprising:
         a) a coolant outflow tube having a lumen in communication with coolant supply means, said coolant outflow tube providing flow of coolant through said lumen from said proximal end towards said surgical distal end of said apparatus;
         b) a coolant return tube providing return of coolant from said surgical distal end towards said proximal end of the apparatus; at least one communicating bore present in the distal end of the apparatus allows passage of coolant from the coolant outflow tube to the coolant return tube; an expansion chamber having a cross-section larger than that of the coolant return tube, said expansion chamber located on the extreme distal end of said coolant return tube,
         said coolant outflow tube being concentrically disposed within said coolant return tube;
      electrically-powered heating means, said heating means raising and regulating the temperature of said apparatus; and
      a thermostat for determining the temperature of the surgical tip;
   wherein said coolant outflow tube further allows introduction of tissue-emulsifying surgical implements so as to extend out through said surgical distal end of said apparatus;
   and said apparatus being electrically connected to:
      a control unit activating said cooling means, and said control unit activating said heating means, such that upon activation of said control unit, coolant flow is induced from said coolant supply means, through said coolant outflow tube towards the distal end of said coolant outflow tube, through said communicating bore into said expansion chamber resulting in lowering the temperature at the expansion chamber to a temperature at which mammalian tissue contacting the expansion chamber would adhere to the apparatus.

2. The apparatus of claim 1, additionally comprising a drill member coupled with a motor, said drill member including a shaft having a distal end and a drill bit at said distal end, said drill member protruding from the center of the surgical tip of said apparatus.

3. The apparatus of claim 2, wherein said drill member is rotatable to a speed of approximately 80,000 RPM.

4. The apparatus of claim 2, wherein said drill member comprises a drill bit having balanced blades with oppositely tapered ends, said blades connected to a crossbar.

5. The apparatus of claim 2, wherein said drill bit and drill shaft are formed of a metal selected from titanium and stainless steel.

6. The apparatus of claim 1, wherein said electrically powered heating means comprise a heat-conductive element included in an electrical circuit, at least a portion of said element located at said surgical tip; wherein activation of electrical current to said circuit results in generation of heat from said element.

7. The apparatus of claim 1, additionally comprising a carrier tube present within the lumen of said coolant outflow tube, and additionally comprising an irrigation fluid source, said carrier tube configured for transport of irrigation fluid to said surgical tip from said irrigation fluid source.

8. The apparatus of claim 7, further comprising a plurality of valves for regulating the flow of irrigation fluid in said apparatus.

9. The apparatus of claim 1, wherein said surgical tip is disposable.

10. The apparatus of claim 1, wherein said coolant outflow tube and said coolant return tube are closed at said respective distal ends, closing said passageway.

11. The apparatus of claim 10, wherein said closed distal ends of said coolant outflow tube and said coolant return tube define a shoulder, extending outward from said apparatus.

12. The apparatus of claim 11, wherein said distal end of said surgical tip extends a distance beyond said shoulder, said distance corresponding to a maximum surgical penetration depth into the human body, for the surgical tip of said apparatus.

13. The apparatus of claim 1, wherein said apparatus further comprises a suction tube present within the lumen of said coolant outflow tube, for providing suction of fluids from said surgical tip; said suction tube being in communication with a suction unit.

14. The apparatus of claim 1, wherein said coolant supply means provides a coolant selected from: compressed carbon dioxide and compressed nitrous oxide.

15. The apparatus of claim 1, further comprising a plurality of valves for regulating the flow of coolant in said apparatus.

16. The apparatus of claim 1, further comprising a coolant outflow line, from which coolant is discharged to the ambient environment after passage through the expansion chamber.

17. The apparatus of claim 1, wherein the surgical tip is formed from a head portion and a core.

18. The apparatus of claim 17, wherein said core is separated from the head portion by an electrically insulating ring and an air gap, such that the head portion and the core can maintain opposing electrical potentials to form an electrical circuit and said head portion and said core are each connected to an opposing terminal on an electrical power supply; wherein said circuit is electrically connected to said heating means.

19. The apparatus of claim 17, wherein said head portion is formed of two members, separated by an O-ring therebetween.

20. The apparatus of claim 19, wherein said O-ring is formed of a polymer, for providing shock absorbance from vibrations.

21. The apparatus of claim 17, wherein said head portion is formed of surgical grade steel, or from plastic having electrically conducting wires therein.

22. The apparatus of claim 1, wherein the temperature at the expansion chamber can reach approximately −5° C. to −10° C. upon flow of coolant flow into said expansion chamber.

23. The apparatus of claim 1, wherein said heating means heat to a temperature of approximately 25° C. to 35° C.

24. A method of use of the apparatus of claim 1 for surgery of tissue within a capsule comprising:
   a) creating a minimal size opening in said capsule using a surgical knife followed by activation of a thermal electrical pulsed burning tool;
   b) providing the apparatus of claim 1,
   c) inserting at least a portion of a drill bit or at least a portion of a phacoemulsification transducer through said opening into said capsule;
   d) contacting the opening in said capsule with the expansion chamber of said apparatus;
   e) cooling said expansion chanter such that sufficient cooling transfers to said capsule allowing for freeze-sealing the opening of said capsule by said apparatus around said drill bit or around said transducer;
   f) activating said heating means, to limit conduction of said cooling toward at least said proximal handle end of said apparatus; g) irrigating said capsule with irrigation fluid to hydrodissect said capsule; h) rotating said drill bit or activating said transducer so as to emulsify at least a portion of said tissue in said capsule; further irrigating said capsule and providing suction to flush away said emulsified tissue;
   i) deactivating said cooling means to allow the temperature of said expansion chamber to rise and said freeze-seal to break;
   j) retracting the apparatus from the capsule.

25. The method of claim 24, wherein the encapsulated tissue in said capsule includes a cataract and said capsule is a lens capsule.

26. The method of claim 25, wherein said creating an opening in said capsule includes creating an opening in said lens capsule proximate to said cataract, and wherein said opening has a maximal length or diameter of 1–3.5 mm in the cornea, and a maximal length or diameter of 2 mm in the lens.

27. The method of claim 24 wherein said contacting the capsule includes positioning said expansion chamber to surround at least a substantial portion of said opening.

28. The method of claim 27, wherein said positioning includes surrounding all of said opening and the periphery surrounding the opening.

29. The method of claim 24, wherein in said step of cooling and freeze-sealing, the temperature at the expansion chamber is lowered to approximately −5° C. to −10° C. upon flow of coolant flow into said expansion chamber.

30. The method of claim 24, wherein in said step of activating said heating means, the temperature of said heating means is raised to approximately 25° C. to 35° C.

31. The method of claim 24, wherein said freeze-sealing of said capsule maintains the integrity of the capsule opening, preventing shearing forces from damaging the capsule and preventing leakage of bodily material from within the capsule.

32. The method of claim 24, additionally comprising pressurizing said surgical site.

33. The method of claim 24, wherein the capsule comprises one of the following pathologies:
   an encapsulated tumor, a meniscus and an encapsulated parasite.

* * * * *